US00PP27173P3

(12) United States Plant Patent
Trees

(10) Patent No.: US PP27,173 P3
(45) Date of Patent: Sep. 20, 2016

(54) ***EPILOBIUM* PLANT NAMED 'DIAMONDBACK'**

(50) Latin Name: *Epilobium canum*
Varietal Denomination: Diamondback

(71) Applicant: Ball Horticultural Company, West Chicago, IL (US)

(72) Inventor: Scott Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 103 days.

(21) Appl. No.: 14/121,709

(22) Filed: Oct. 9, 2014

(65) Prior Publication Data

US 2015/0351299 P1 Dec. 3, 2015

Related U.S. Application Data

(60) Provisional application No. 61/997,519, filed on Jun. 3, 2014.

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

(56) References Cited

PUBLICATIONS

Reid et al., Progress Report 2012-2013, http://ucanr.edu/sites/SaratogaHort/files/164132.pdf.*

* cited by examiner

*Primary Examiner* — Anne Grunberg
(74) *Attorney, Agent, or Firm* — Audrey Charles

(57) ABSTRACT

A new and distinct cultivar of *Epilobium* plant named 'Diamondback', characterized by its medium red-orange colored flowers, dark green-colored foliage, and moderately vigorous, mounded-trailing growth habit, is disclosed.

1 Drawing Sheet

Latin name of genus and species of plant claimed: *Epilobium canum.*

Variety denomination: 'Diamondback'.

BACKGROUND OF THE INVENTION

The present invention relates to a new and distinct cultivar of *Epilobium* plant botanically known as *Epilobium canum* and hereinafter referred to by the cultivar name 'Diamondback'.

The new cultivar originated in a controlled breeding program in Guadalupe, Calif. during August 2011. The objective of the breeding program was the development of *Epilobium* cultivars with attractive flower coloration and a moderately vigorous, mounded-trailing growth habit.

The new *Epilobium* cultivar is the result of open-pollination. The female (seed) parent of the new cultivar is the proprietary *Epilobium canum* breeding selection coded ZAU-109, not patented, characterized by its white-colored flowers, medium green-colored foliage, and vigorous, semi-upright, mounded growth habit. The male (pollen) parent of the new cultivar is unknown. The new cultivar was discovered and selected as a single flowering plant within the progeny of the above stated open-pollination during September 2012 in a controlled environment in Guadalupe, Calif.

Asexual reproduction of the new cultivar by terminal stem cuttings since September 2012 in Guadalupe, Calif. and Arroyo Grande, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Diamondback' as a new and distinct cultivar of *Epilobium* plant:

1. Medium red-orange colored flowers;
2. Dark green-colored foliage; and
3. Moderately vigorous, mounded-trailing growth habit.

Plants of the new cultivar differ from plants of the female parent primarily in flower color and growth habit.

Of the many commercially available *Epilobium* cultivars, the most similar in comparison to the new cultivar is 'Sidewinder', U.S. Plant patent application Ser. No. 13/998,155. However, in side by side comparisons, plants of the new cultivar differ from plants of 'Sidewinder' in at least the following characteristics:

1. Plants of the new cultivar have larger leaves, as measured by length and width, than plants of 'Sidewinder';
2. Plants of the new cultivar have a lighter flower color, than plants of 'Sidewinder'; and
3. Plants of the new cultivar have darker green foliage than plants of 'Sidewinder'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Diamondback'. The plants were grown in a one-gallon container for three months in a greenhouse in West Chicago, Ill.

DETAILED BOTANICAL DESCRIPTION

Figure 1:
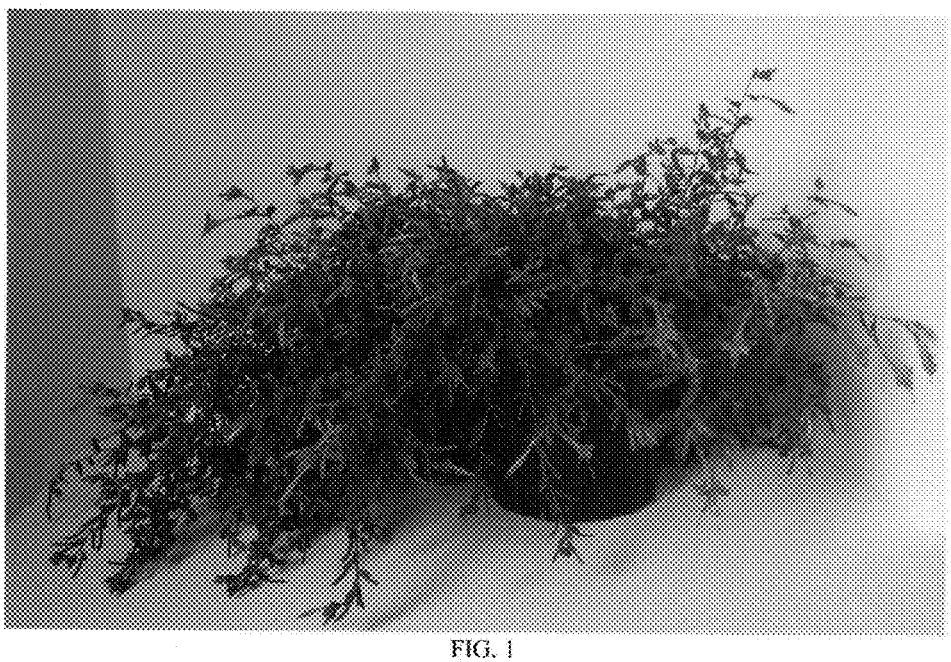
FIG. 1 illustrates a side view of the overall growth and flowering habit of 'Diamondback'.
Figure 2:
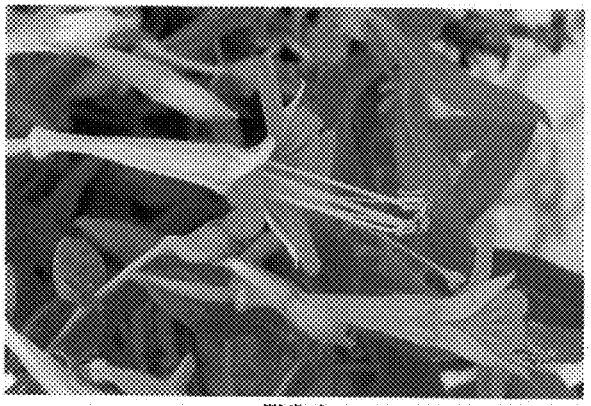
FIG. 2 illustrates a close-up view of an individual flower of 'Diamondback'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in September 2014 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. a one-gallon container for three months utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Epilobium canum* cultivar Diamondback.

Parentage:

*Female parent*.—Proprietary *Epilobium canum* breeding selection coded ZAU-109, not patented.

*Male parent*.—Unknown.

Propagation:

*Type cutting*.—Terminal stem.

*Time to initiate roots*.—Approximately 10 to 14 days.

*Time to produce a rooted cutting*.—Approximately 16 to 20 days.

*Root description*.—Fibrous, moderately thick, and brown in color.

*Rhizome description*.—Width: Approximately 3.0 mm. Color: Closest to but lighter than 200D.

*Rooting habit*.—Freely branching.

Plant description:

*Commercial crop time*.—Approximately 26 to 34 weeks from a rooted cutting to finish in a 2.25 inch pot.

*Growth habit and general appearance*.—Moderately vigorous, mounded-trailing.

*Size*.—Height from soil level to top of plant plane: Approximately 17.0 cm. Width: Approximately 65.0 cm.

*Branching habit*.—Freely branching, pinching enhances basal branching. Quantity of main branches per plant: Approximately 11.

*Lateral branch*.—Strength: Strong. Length: Approximately 33.0 cm. Diameter: Approximately 3.0 mm. Length of central internode: Approximately 1.5 cm. Texture: Densely pubescent. Color of young stem: 138B. Color of mature stem: 138B, with age becomes woody 199B.

Foliage description:

*General description*.—Quantity of leaves per main branch: Approximately 20, leaves abscised on woody portions. Fragrance: None detected. Form: Simple. Arrangement on flowering stem: Alternate.

*Leaves*.—Aspect: Obtuse angle to stem. Shape: Elliptic. Margin: Entire. Apex: Broadly acute. Base: Sessile. Venation pattern: Pinnate. Length of mature leaf: Approximately 3.5 cm. Width of mature leaf: Approximately 1.0 cm. Texture of upper and lower surfaces: Densely pubescent. Color of upper surface of young and mature foliage: 137A with midvein of 147D. Color of lower surface of young and mature foliage: 137B with midvein of 147D.

Flowering description:

*Flowering habit*.—'Diamondback' flowers outdoors late summer through fall.

*Lastingness of individual flower on the plant*.—Approximately 7 to 10 days.

Flower description:

*General description*.—Type: Single, funnel shaped with a basal bulge, sessile. Quantity per plant: Approximately 40. Fragrance: None detected.

*Bud*.—Rate of opening: Generally takes 5 to 7 days for bud to progress from first color to fully open flower. Quantity per plant: Approximately 50.

*Bud just before opening*.—Shape: Ellipsoid with a basal bulge. Length: Approximately 3.5 cm. Diameter: Approximately 5.0 mm. Texture: Densely glandular pubescent. Color: 145A with an overlay of 35B.

*Corolla*.—Depth: Approximately 3.5 cm. Diameter: Approximately 2.1 cm.

*Petals*.—Quantity: 4, fused to form a tube. Shape: Obovate. Margin: Entire. Apex: Bifid with rounded lobes. Length from tube: Approximately 9.0 mm. Width: Approximately 8.0 mm. Texture of upper and lower surfaces: Glabrous. Color of upper surface when first and fully open: 35A with venation of N34A. Color of lower surface when first and fully open: 35B with venation of N34A.

*Corolla tube*.—Length: Approximately 2.0 cm. Diameter at distal end: Approximately 6.0 mm. Diameter at proximal end: Approximately 3.0 mm. Texture of inner surface: Glabrous. Texture of outer surface: Densely glandular pubescent. Color of inner surface: 37D. Color of outer surface: 35C.

*Sepals*.—Quantity per flower: 4. Shape: Elliptic, lower three quarters fused to petals. Margin: Entire. Apex: Acute. Length: Approximately 3.4 cm. Length of free portion: Approximately 1.0 cm. Width: Approximately 3.0 mm. Texture of inner surface: Glabrous. Texture of outer surface: Densely glandular pubescent. Color of inner surface: 37D with 145B at tip. Color of outer surface: 35C with tips of 145B.

*Reproductive organs*.—Androecium: Stamen quantity: 8. Stamen length: Approximately 4.2 cm. Filament length of fixed portion: Approximately 2.2 cm. Filament color: 37A. Anther shape: Bilobed. Anther length: Approximately 2.0 mm. Anther color: Between N34A and N34B. Pollen amount: Moderate. Pollen color: 11D. Gynoecium: Pistil quantity: 1 per flower. Pistil length: Approximately 6.3 cm. Stigma shape: 4-lobed, flattened. Stigma length: Approximately 1.0 mm. Stigma color: N34A. Style length: Approximately 4.4 cm. Style color: 34A. Ovary length: Approximately 1.8 cm. Ovary texture: Densely glandular pubescent. Ovary color: 144B.

Seed and fruit production: Neither seed nor fruit production has been observed.

Disease and pest resistance: Resistance to pathogens and pests common to *Epilobium* has not been observed.

What is claimed is:

1. A new and distinct cultivar of *Epilobium* plant named 'Diamondback', substantially as herein shown and described.

* * * * *